(12) United States Patent
Welsh et al.

(10) Patent No.: US 8,486,987 B2
(45) Date of Patent: Jul. 16, 2013

(54) MECHANISM-BASED SMALL-MOLECULE PARASITE INHIBITORS

(75) Inventors: William J. Welsh, Princeton, NJ (US); Sandhya Kortagere, Newtown, PA (US); Lawrence W. Bergman, Lansdale, PA (US); Akhil B. Vaidya, Wynnewood, PA (US)

(73) Assignees: University of Medicine and Dentistry of New Jersey, Somerset, NJ (US); Philadelphia Health and Education Corporation, Philadelphia, PA (US)

( * ) Notice: Subject to any disclaimer, the term of this patent is extended or adjusted under 35 U.S.C. 154(b) by 216 days.

(21) Appl. No.: 12/743,306

(22) PCT Filed: Nov. 16, 2008

(86) PCT No.: PCT/US2008/083715
§ 371 (c)(1),
(2), (4) Date: Mar. 8, 2011

(87) PCT Pub. No.: WO2009/065096
PCT Pub. Date: May 22, 2009

(65) Prior Publication Data
US 2011/0172268 A1    Jul. 14, 2011

Related U.S. Application Data

(60) Provisional application No. 61/003,509, filed on Nov. 16, 2007.

(51) Int. Cl.
*A61K 31/415* (2006.01)
*A61P 33/02* (2006.01)

(52) U.S. Cl.
USPC ............................. 514/407; 514/359; 514/385

(58) Field of Classification Search
USPC .......................................... 514/407, 359, 385
See application file for complete search history.

(56) References Cited

U.S. PATENT DOCUMENTS

| 7,084,280 B2 | 8/2006 | Ducray et al. |
| 2005/0203067 A1 | 9/2005 | Hresko et al. |

OTHER PUBLICATIONS

De Paulis, "Substituent Effects of N-(1,3-Diphenyl-1H-pyrazol-5-yl)benzamides on Positive Allosteric Modulation of the Metabotropic Glutamate-5 Receptor in Rat Cortical Astrocytes", J. Med. Chem., 2006, 49, pp. 3332-3344.*

* cited by examiner

*Primary Examiner* — Sreeni Padmanabhan
*Assistant Examiner* — Sahar Javanmard
(74) *Attorney, Agent, or Firm* — Fox Rothschild LLP

(57) ABSTRACT

Methods for preventing or treating an Apicomplexan parasite infection in a patient administering to a patient in need thereof an effective amount of a compound of Formulas I-IV.

8 Claims, 12 Drawing Sheets

| | | | |
|---|---|---|---|
| 2-10<br>>100μM | | 2-11<br>>100μM | |
| 2-12<br>136nM | | 2-13<br>336nM | |
| 2-14<br>1-10μM | | 2-15<br><1μM | |
| 2-16<br>1-10μM | | 2-17<br>1-10μM | |
| 2-18<br>1-10μM | | 2-19<br>282nM | |
| 2-20<br>10-100μM | | 2-21<br>342nM | |

MECHANISM-BASED SMALL-MOLECULE PARASITE INHIBITORS

CROSS-REFERENCE TO RELATED APPLICATIONS

This application is a National Stage filing under 35 U.S.C. §371(c) of International application Ser. No. PCT/US08/83715 which claims priority under 35 U.S.C. §119(e) to U.S. Provisional Application Ser. No. 61/003,509, which was filed on Nov. 16, 2007, the disclosure of which is incorporated herein by reference.

BACKGROUND OF THE INVENTION

The Apicomplexan protozoa are a phylum of diverse obligate intracellular parasites. Infection by Apicomplexan parasites causes incalculable morbidity and mortality to mammals such as humans and agricultural animals. Apicomplexan species, such as *Plasmodium, Babesia, Cryptosporidium, Isospora, Cyclospora, Sarcocystis*, and *Toxoplasma*, produce disease of varying severity.

*Toxoplasma* is responsible for diseases throughout the world (except extremely cold or dry climates) and tends to be more prevalent in tropical climates. Serologic studies have shown prevalence rates up to 70% by the age of 25 in some central American populations. In the United States an estimated 0.5-1% of the population becomes infected each year and prevalence ranges from 10-25% by the age of 25.

Although toxoplasmosis is most often a benign disease, noted exceptions are in the cases of congenital infection or immunocompromised individuals. Congenital toxoplasmosis is particularly severe and occurs in one of every one thousand births. Infection can result in spontaneous abortion, premature birth, or full-term with or without progressive disease. Typical congenital toxoplasmosis disease manifestations include retinochoroiditis, intracerebral calcification, hydrocephaly, microcephaly, and psychomotor disturbances. Clinical outcomes indicate 5-10% death, 8-10% severe brain or eye damage, 10-13% moderate-to-severe visual handicaps, 58-72% asymptomatic at birth, developing, retinochoroiditis or mental handicaps later in life.

Toxoplasmosis has been long noted as an opportunistic infection in regards to reactivation of latent infections due to immunosuppression associated with organ transplants and certain cancer treatments. During the 1980s toxoplasmic encephalitis emerged as a common complication associated with AIDS. Early symptoms of toxoplasmic encephalitis can include headache, fever, lethargy, and altered mental status with progression to focal neurological deficits and convulsions. The disease is almost always due to a reactivation of a latent infection and tends to remain confined to the central nervous system. The focal lesions are caused by the destruction of host cells in the immediate vicinity. Other forms of the reactivated disease, especially retinochoroiditis, pneumonitis, myocarditis and myositis, may occasionally occur in conjunction with immunosuppression. *Toxoplasma gondii* is a significant opportunistic pathogen in immunocompromised individuals such as those infected by HIV-AIDS.

*Eimeria*, pathogens of chicken and cattle, *Theileria*, tick-borne parasites of cattle in Africa, and *Cryptosporidium*, an animal parasite as well as an opportunistic pathogen of humans, are members of the phylum. Babesiosis is a rare zoonotic infection transmitted by ticks. The etiological agents, *Babesia* species, are blood parasites which infect a wide variety of wild and domestic animals throughout the world. *Babesia* and *Theileria* form a group called the piroplasms, in reference to intraerythrocytic forms that are pear-shaped in some species. Piroplasms cause tremendous losses of livestock in endemic areas.

*Plasmodium* is the causative agent in malaria. Malaria is the most common and deadly parasitic disease in the world. In any given year, there will be 300-500 million cases of malaria and 1-3 million human fatalities, and about 400 million people are infected. (Trigg, P. I., and A. V. Kondrachine (1998) The Current Global Malaria Situation, Chapter 2, p. 11-22, in MALARIA PARASITE BIOLOGY, PATHOGENESIS AND PROTECTION. Ed. I. W. Sherman, ASM Press, Washington, D.C.) The global situation continues to worsen due to the lack of availability of effective drugs, because there is no effective vaccine for malaria, and because the responsible parasite *Plasmodium* has rapidly developed resistance to all currently available drugs. In an increasingly wide geographic area, both *Plasmodium falciparum* and *Plasmodium vivax* have been developing resistance to chloroquine, the most successful antimalarial drug in the past several decades. Mefloquine and doxycycline, the two other frontline drugs for the treatment and prevention of malaria are becoming increasingly ineffective. (See Vroman, J. A. et al. (1999) Curr. Pharm. Design 5:101-138.) Artemisinin analogs such as artesunate and arteether were later introduced that are found to be quite effective, particularly against drug-resistant *P. falciparum* but observations of drug-induced and dose-related neurotoxicity in animals have raised concern about the safety of these compounds for human use. (See Bhattacharjee, A. K. and J. M. Karle (1999) Chem. Res. Toxicol. 12: 422-428 and Genovese, R. F. and D. B. Newman (2008) Arch. Toxicol. 82 (6):379-85.)

Several protozoa parasites are listed as Category B biodefense targets by the National Institute for Allergy and Infectious Diseases (NIAID), including *Cryptosporidium parvum, Cyclospora cayatanensis*, and *Toxoplasma*. *Cyclospora cayatanensis* and *Cryptosporidium parvum* cause severe persistent diarrhea. The phylum also includes gregarines, parasites of the guts of invertebrates including cockroaches and shrimp. These protozoan parasites share distinctive morphological features, cytoskeletal organization, and modes of replication, motility, and invasion.

Infection by Apicomplexan parasites causes serious infectionsin healthy people, but are extremely dangerous and often deadly in immunocompromised individuals (e.g., HIV/AIDS patients, organ recipients, people undergoing chemotherapy), in children and the elderly, and in pregnant women. They also pose imminent threats to homeland security as agents of bioterrorism, since infections are readily spread via contaminated food and water. Vaccines are non-existent, and adequate drug treatment is lacking due to acquired drug resistance by these parasites and severe adverse reactions by patients to existing treatments (e.g., sulfa drugs). For these reasons, these infections are designated as "Biowarfare Pathogens" by the National Institutes of Health (NIH).

Toxoplasmosis is the leading cause of severe congenital neurological defects (brain and eye damage) in humans, and is a frequent cause of still births and spontaneous abortions. Toxoplasmosis is also a very serious opportunistic infection that causes blindness and life-threatening meningitis in immuno-compromised individuals. Toxoplasmosis is still an important opportunistic infection of the central nervous system in patients infected with HIV/AIDS. (Hoffmann, C., et al. (2007) Clin. Microbial Infect. 13:510-515.) Approximately 10% of AIDS patients in the USA and up to 30% in Europe were estimated to die from toxoplasmosis in 2005 (Davaro, R. E. and A. Thirumalai (2007) J. Intensive Care Med. 22 (2): 73-81.)

Since the introduction of highly active antiretroviral therapy (HAART), the rates of opportunistic infections have dropped markedly as has overall morbidity and mortality from HIV infection in developed countries. However, opportunistic infections remain the most important cause of death in HIV-infected people due to both late presentation of HIV infections and failure of HAART to adequately restore cell-mediated immunity in all individuals. Persistent neurological deficits are often present in surviving patients (Hoffmann, C., et al. (2007) Clin. Microbial Infect. 13:510-515) and lifelong maintenance therapy is needed to prevent recurrent opportunistic infection (Manzardo, C., et al. (2005) J. Neurovirol. 11 Suppl 3:72-82.) For those patients who fail HAART, those who are unable to tolerate it, or those whose treatments are interrupted, therapy against opportunistic infections remains essential.

Reemergence of toxoplasmosis as a life-threatening disease in HIV/AIDS patients is anticipated in the wake of emerging multi-drug resistant strains of HW (Omrani, A. S. and D. Pillay (2000) Hosp. Med. 61 (5):304-5; Omrani, A. S. and D. Pillay (2000) J. Infect. 41 (1):5-11.) Toxoplasmic encephalitis in those with AIDS in the developing world remains a frequent and devastating problem. Encephalitis is the most serious manifestation of toxoplasmosis in immuno-suppressed patients as it causes severe neurologic and rapidly fatal damage to such patients (Hill, D. and J. P. Dubey (2002) Clin. Microbiol. Infect. 8 (10):634-40.) Toxoplasmic chorioretinitis is less frequent than toxoplasmic encephalitis in patients with AIDS but both have serious morbidity. Cerebral toxoplasmosis is the most common neurological mass lesion in patients with AIDS (Hoffmann, C., et al. (2007) Clin. Microbial Infect. 13:510-515; Cohen, B. A. (1999) Semin. Neurol. 19 (2):201-11; Simpson, D. M. and M. Tagliati (1994) Ann. Intern. Med. 121 (10):769-85.) Treatments for Toxoplasmosis exist, however their failure to kill the parasitic cysts leads to frequent relapses and their toxicity often forces discontinuation of the drug.

Cryptosporidiosis (Crypto) is a leading cause of water-borne disease in humans worldwide. Crypto causes an astounding 500 million cases of diarrhea annually, which is especially serious and often fatal in immuno-compromised individuals. Crypto-associated diarrhea is also a widespread problem in the cattle industry. At least 45 serious outbreaks of Crypto were reported in the USA during the past 20 years, including a massive outbreak in 1993 when over 300,000 people in Milwaukee became gravely ill and scores died. The Crypto parasite is resistant to disinfectants such as chlorine bleach; thus it can survive in chlorinated swimming pools and water parks. There is no known effective therapy for human Cryptosporidiosis.

Cyclosporiasis, which causes prolonged diarrhea and other gastrointestinal problems in humans, is especially severe and sometimes deadly in immuno-compromised individuals (e.g., HIV/AIDS patients). Although therapeutic treatments currently exist, many of them are contraindicated for pregnant women, the elderly, and in people with hepatic and renal impairment. No alternative drugs have been identified to date for people who are unable to take sulfa drugs.

In view of the serious global threat posed by these Apicomplexan-related diseases, there is an urgent unmet need for safe and effective medicines that are useful for prophylaxis and treatment. There is a further urgent unmet need for pesticides against Apicomplexan parasites. There is still a further unmet urgent need for agents for use against several protozoa parasite biodefense targets listed as Category B agents by the NIAID.

SUMMARY OF THE INVENTION

There is provided, in accordance with the present invention, a method for preventing or treating an Apicomplexan parasite infection in a patient by administering to a patient in need thereof an effective amount of a compound of Formula I:

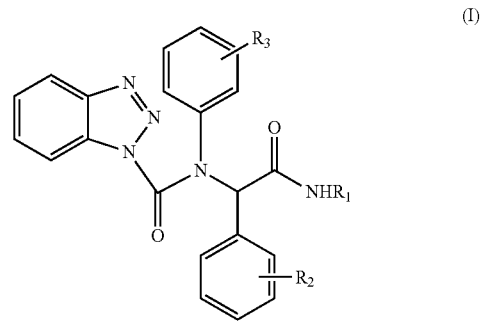

wherein $R_1$, $R_2$, and $R_3$ are independently selected from hydrogen, halogen, acetoxy, lower alkyl, aryl, and lower alkoxy.

Also provided is a method for preventing or treating an Apicomplexan parasite infection in a patient by administering to a patient in need thereof an effective amount of a compound of Formula II:

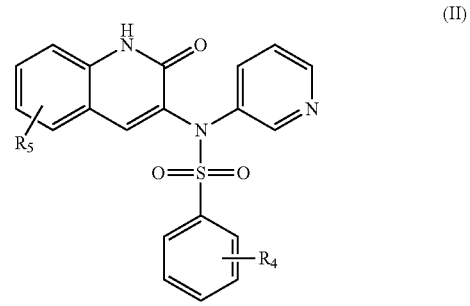

wherein $R_4$ and $R_5$ are independently selected from hydrogen, halogen, acetoxy, lower alkyl, aryl, and lower alkoxy.

Also provided is a method for preventing or treating an Apicomplexan parasite infection in a patient by administering to a patient in need thereof an effective amount of a compound of Formula III:

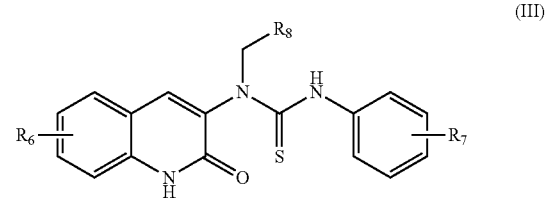

wherein $R_6$ and $R_7$ are independently selected from hydrogen, halogen, acetoxy, lower alkyl, aryl, and lower alkoxy; and $R_8$ is a 5- or 6-membered aromatic ring, including a heteroaromatic ring having from 1 to 3 heteroatoms selected from N, O and S.

Also provided is a method for preventing or treating an Apicomplexan parasite infection in a patient by administering to a patient in need thereof an effective amount of a compound of Formula IV:

(IV)

wherein $R_9$, $R_{10}$, and $R_{11}$ are independently selected from hydrogen, halogen, acetoxy, lower alkyl, lower haloalkyl, lower haloalkoxy, aryl, and lower alkoxy;

$R_{12}$ is a bond or —HC=N—; and $R_{13}$ is selected from methyl, —C(CH$_3$)$_3$, —NHC(CH$_3$)$_3$, —C≡N, hydroxyl, wherein $R_{14}$ is selected from hydrogen, halogen, acetoxy, lower alkyl, lower haloalkyl, lower haloalkoxy, aryl, and lower alkoxy and n is an integer from 1 to 3.

In one embodiment, the compound is a compound of Formula VI:

(VI)

In another embodiment, the compound is selected from:

(VII)

(VIII)

(IX)

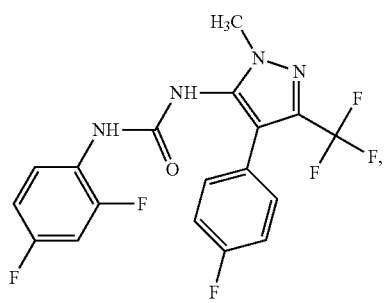
(X)

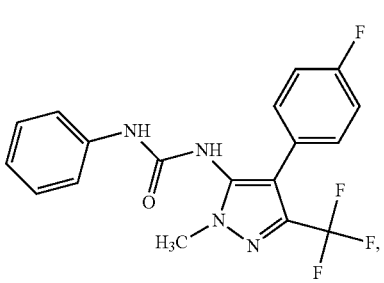
(XI)

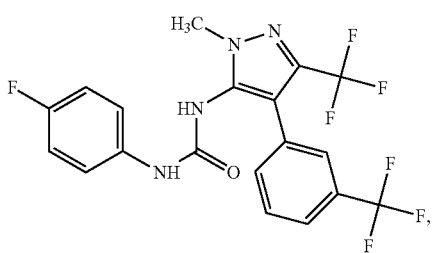
(XII)

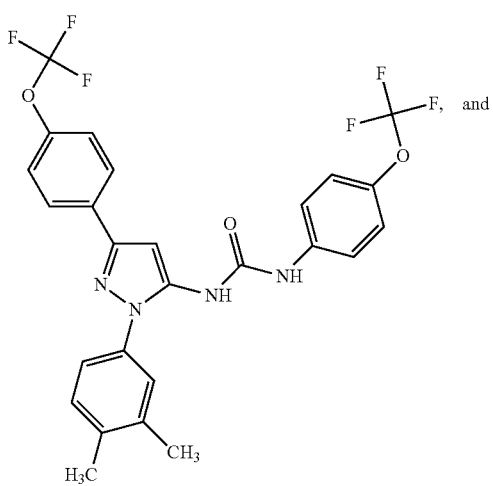
(XIII)

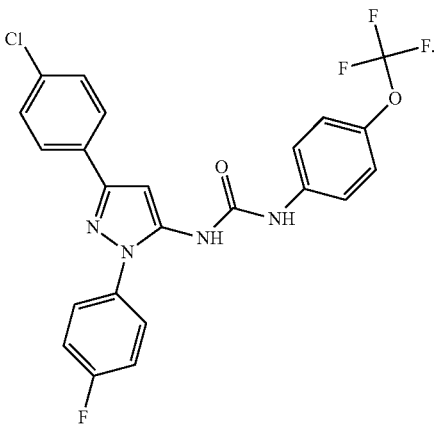
(XIV)

In yet another embodiment, the Apicomplexan parasite is selected from *Toxoplasma, Plasmodium, Eimeria, Theileria, Babesia, Sarcocystis, Cryptosporidium, Cydospora, Isospora,* and *Neospora.*

In an additional embodiment, the Apicomplexan parasite is selected from *Plasmodium falciparum, Plasmodium vivax, Cryptosporidium parvum,* and *Cyclospora cayatanensis.*

DETAILED DESCRIPTION OF THE INVENTION

MTIP protein is a member of the myosin family of proteins and is distantly related to myosin light chain in higher organisms and also to the calcium binding protein calmodulin. MyoA protein is however very unique to the apicomplexans and in complex with MTIP promotes gliding motility among apicomplexans. This feature of gliding motility is highly important for the parasites to attack red blood cells and use their machinery to reproduce and form the infective sporozoites. The strategy used was to disrupt the formation of the protein-protein complex between MTIP and MyoA.

Figure 1:
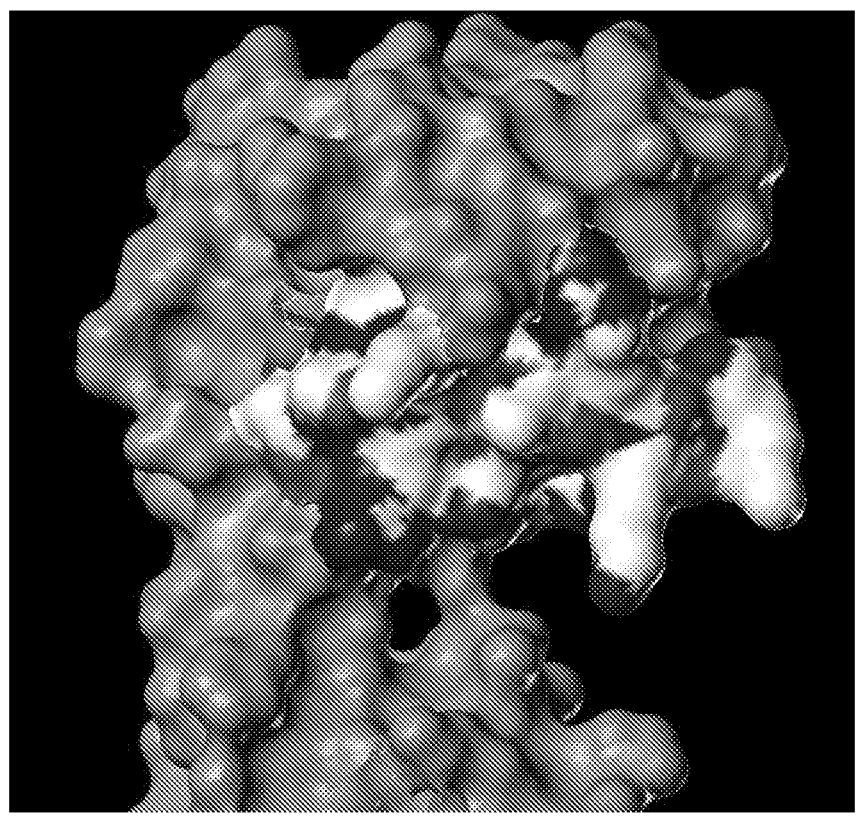
FIG. 1 is a surface representation of the crystal structure complex of MTIP chain-C with MyoA tail peptide.

MyoA binds to MTIP with an affinity of 85 μM. Recently the crystal structure of the MTIP in complex with MyoA was solved (Protein Data Bank (PDC) code-2AUC). The crystal structure shows MTIP as composed of three identical subunits, while only the C subunit interacts with the MyoA protein. The MyoA protein consists of thirteen amino acids forming an alpha helix and is placed in the grove of the MTIP-C subunit. (FIG. 1). The interactions of MyoA with MTIP-C are mainly non-bonded interactions with the hydrophobic helix occupying the complete binding site of MTIP. Also, Gln808, His810 and Arg812 of MyoA form hydrogen bonded interactions with the main chain oxygen and nitrogen atoms of Trp172, Asp174, Ala175, and Ile203. Biochemical evidence of single and cassette mutation of Leu804, Val807, Ile811 and Arg812 of MyoA to Ala have led to the loss of interaction with MTIP.

Using this structural information of interaction between MyoA and MTIP, small molecule inhibitors were designed that could either competitively inhibit MyoA interaction or disrupt the MTIP-MyoA (protein-protein) complex. It was discovered that a select set of compounds which share three-dimensional chemical attributes are effective agents against Apicomplexa species. Surprisingly, classes of organic compounds not previously known for anti-parasitic activity, were found to be potent inhibitors of the growth of Apicomplexa species.

As used herein the following terms, unless otherwise indicated, shall be understood to have the following meanings:

"Patient" means a mammal including a human, agricultural animal, or companion animal.

"Effective amount" means an amount of a compound of the present invention having an $IC_{50}$<10 μM, and thus producing the desired therapeutic effect, wherein the $IC_{50}$ value is determined by a compound's effect on parasite growth in mammalian (e.g. human) red cells as measured by incorporation of a labeled compound (e.g. $^3$H-labeled hypoxanthine) in the parasite.

"Treat" or "treatment" or "treating" mean to lessen, eliminate, inhibit, improve, alter, or prevent a disease or condition, for example by administration of compound of the present invention.

"Pharmaceutically acceptable" means methods, procedures, formulations, addition salts, solutions, preparations, and routes of administration known by those with skill in the art to be proper and safe in the practice of administering biologically active medicaments to patients.

"Alkyl" means aliphatic hydrocarbon group which may be branched or straight-chained having about 1 to about 10 carbon atoms. A subclass of alkyl is "lower alkyl" having about 1 to about 5 carbon atoms. Branched means that one or more lower alkyl groups such as methyl, ethyl, or propyl are attached to a linear alkyl chain. The alkyl group is also optionally substituted by alkoxy, halo, carboxy, or hydroxy. Examples of alkyl include methyl, fluoromethyl, difluoromethyl, trifluoromethyl, ethyl, n-propyl, isopropyl, butyl, sec-butyl, t-butyl, amyl and hexyl.

"Halo" means fluoro, chloro, bromo, or iodo.

"Aryl" means aromatic carbocyclic radical containing about 6 to about 10 carbon atoms. Exemplary aryl include phenyl or naphthyl, or phenyl or naphthyl substituted with one or more aryl group substituents which may be the same or different, where "aryl group substituent" includes hydrogen, hydroxy, halo, alkyl, alkoxy, carboxy, or alkoxycarbonyl.

"Alkoxy" means an alkyl-O— group in which the alkyl group is as previously described. The alkoxy group may be optionally substituted by one or more alkoxy, carboxy, alkoxycarbonyl, or carboxyaryl. Exemplary alkoxy groups include methoxy, ethoxy, n-propoxy, i-propoxy, n-butoxy, heptoxy, 2-(morpholin-4-yl)ethoxy and 2-(ethoxy)ethoxy.

This invention relates to methods for preventing or treating an Apicomplexan parasite infection in a patient by administering to a patient in need thereof an effective amount of a compound of Formulas I-IV. Any Apicomplexan parasite that can be inhibited with a compound of Formulas I-IV is a suitable parasite to be targeted by the methods of the present invention. In one embodiment, the Apicomplexan parasite is selected from *Toxoplasma, Plasmodium* (e.g. *Plasmodium falciparum* and *Plasmodium vivax*), *Eimeria, Theileria, Babesia, Sarcocystis, Cryptosporidium, Cydospora, Isospora*, and *Neospora.*

This invention also relates to using compounds of Formulas I-IV against biodefense targets, particularly protozoa parasites listed as Category B agents by the NIAID. In one embodiment, the parasite is selected from *Cryptosporidium parvum, Cyclospora cayatanensis*, and *Toxoplasma* and the method includes administering to a patient in need thereof an effective amount of a compound of Formulas I-IV to prevent or treating a parasite infection in the patient.

Compounds of Formula I-IV can also be used as pesticides to combat Apicomplexan parasites.

Compounds utilized in the methods of the present invention include effective compounds within the following formulas:

Formula I:

(I)

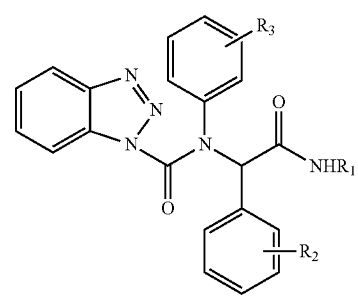

wherein $R_1$, $R_2$, and $R_3$ are independently selected from hydrogen, halogen, acetoxy, lower alkyl, aryl, and lower alkoxy;

Formula II:

(II)

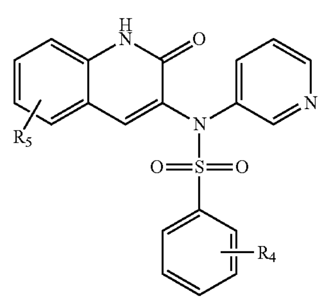

wherein $R_4$ and $R_5$ are independently selected from hydrogen, halogen, acetoxy, lower alkyl, aryl, and lower alkoxy;

Formula III:

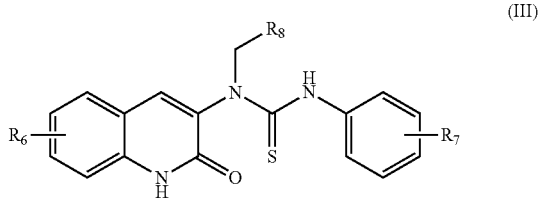

wherein $R_6$ and $R_7$ are independently selected from hydrogen, halogen, acetoxy, lower alkyl, aryl, and lower alkoxy; and $R_8$ is a 5- or 6-membered aromatic ring, including a heteroaromatic ring having from 1 to 3 heteroatoms selected from N, O and S; and Formula IV:

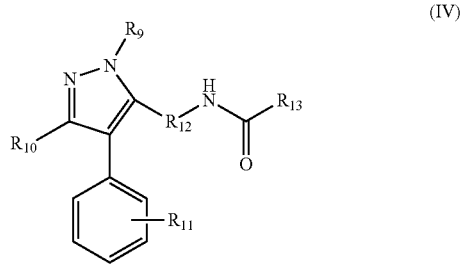

wherein $R_9$, $R_{10}$, and $R_{11}$ are independently selected from hydrogen, halogen, acetoxy, lower alkyl, lower haloalkyl, lower haloalkoxy, aryl, and lower alkoxy;

$R_{12}$ is a bond or —HC=N—;

$R_{13}$ is selected from methyl, —C(CH$_3$)$_3$, —NHC(CH$_3$)$_3$, —C≡N, hydroxyl,

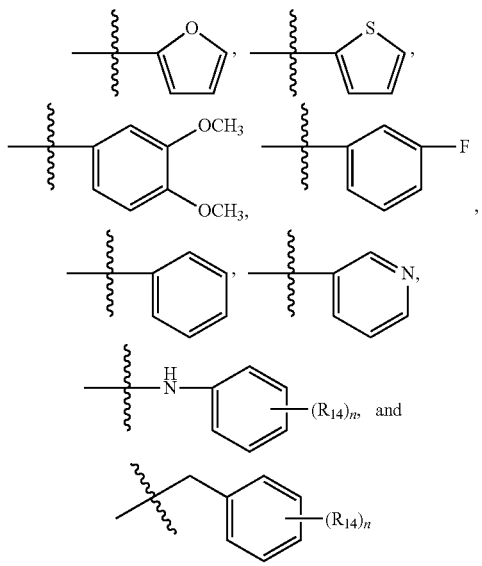

wherein $R_{14}$ is selected from hydrogen, halogen, acetoxy, lower alkyl, lower haloalkyl, lower haloalkoxy, aryl, and lower alkoxy and n is an integer from 1 to 3.

The compounds utilized in the present invention may be prepared by methods familiar to one of ordinary skill in the art. Compounds of the present invention are also available from commercial sources, including Ryan Scientific, Inc. (Mt. Pleasant, S.C.), Maybridge (Thermo Fisher Scientific, Inc.) (Cornwall, UK), and Asinex Inc. (Winston-Salem, N.C.).

Also provided are pharmaceutical compositions that include an effective amount of a compound of Formulas I-IV and a pharmaceutically acceptable carrier.

In practice, a composition containing a compound of Formulas I-IV may be administered in any variety of suitable forms, for example, by inhalation, topically, parenterally, rectally, or orally. More specific routes of administration include intravenous, intramuscular, subcutaneous, intraocular, intrasynovial, colonical, peritoneal, transepithelial including transdermal, ophthalmic, sublingual, buccal, dermal, ocular, nasal inhalation via insufflation, and aerosol.

A composition containing a compound of Formulas I-IV may be presented in forms permitting administration by the most suitable route. The invention also relates to administering compositions containing a compound of Formulas I-IV, which is suitable for use as a medicament in a patient. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of oral dosage forms, or injectable solutions, or suspensions.

The choice of vehicle and the compound of Formulas I-IV in the vehicle are generally determined in accordance with the solubility and chemical properties of the product, the particular mode of administration and the provisions to be observed in pharmaceutical practice. When aqueous suspensions are used they may contain emulsifying agents or agents which facilitate suspension. Diluents such as sucrose, ethanol, polyols such as polyethylene glycol, propylene glycol and glycerol, and chloroform or mixtures thereof may also be used. In addition, the compound of Formulas I-IV may be incorporated into sustained-release preparations and formulations.

For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The injectable forms must be fluid to the extent that it can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The solutions of the salts of the products according to the invention are especially useful for administration by intramuscular or subcutaneous injection. Solutions of the compound of Formulas I-IV as a free base or pharmacologically acceptable salt can be prepared in water suitably mixed with a surfactant such as hydroxypropyl-cellulose. Dispersion can also be prepared in glycerol, liquid polyethylene glycols, and mixtures thereof and in oils. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation, microfiltration, and/or by various antibacterial and antifungal agents, for example, parabens, chlorobutanol, phenol, sorbic acid, thimerosal, and the like.

Sterile injectable solutions are prepared by incorporating the compound of Formulas I-IV in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the methods of preparation include, but are not limited to, vacuum drying and the freeze drying technique, which yield a powder of the active ingredient plus any additional desired ingredient from previously sterile-filtered solution thereof.

Topical administration, gels (water or alcohol based), creams or ointments containing the compound of Formulas I-IV may be used. The compound of Formulas I-IV may be also incorporated in a gel or matrix base for application in a patch, which would allow a controlled release of compound through transdermal barrier.

For administration by inhalation, the compound of Formulas I-IV may be dissolved or suspended in a suitable carrier for use in a nebulizer or a suspension or solution aerosol, or may be absorbed or adsorbed onto a suitable solid carrier for use in a dry powder inhaler.

The percentage of compound of Formulas I-IV in the compositions used in the present invention may be varied, it being necessary that it should constitute a proportion such that a suitable dosage shall be obtained. Obviously, several unit dosage forms may be administered at about the same time. A dose employed may be determined by a physician or qualified medical professional, and depends upon the desired therapeutic effect, the route of administration and the duration of the treatment, and the condition of the patient. A therapeutically effective dose of a compound of Formulas I-IV which is determined by a qualified medical professional to prevent, mollify, lessen the severity of, cure, or otherwise control malaria in humans, may vary depending upon the nature of the patient and the severity of the disease and the route of administration. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 10, mg/kg body weight per day by intravenous administration. In each particular case, the doses are determined in accordance with the factors distinctive to the patient to be treated, such as age, weight, general state of health and other characteristics, which can influence the efficacy of the compound according to the invention.

The compound of Formulas I-IV used in the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the compound of Formulas I-IV may be administered 1 to 4 times per day. Of course, for other patients, it will be necessary to prescribe not more than one or two doses per day.

EXAMPLES

Example 1

Design Strategy

Figure 2:
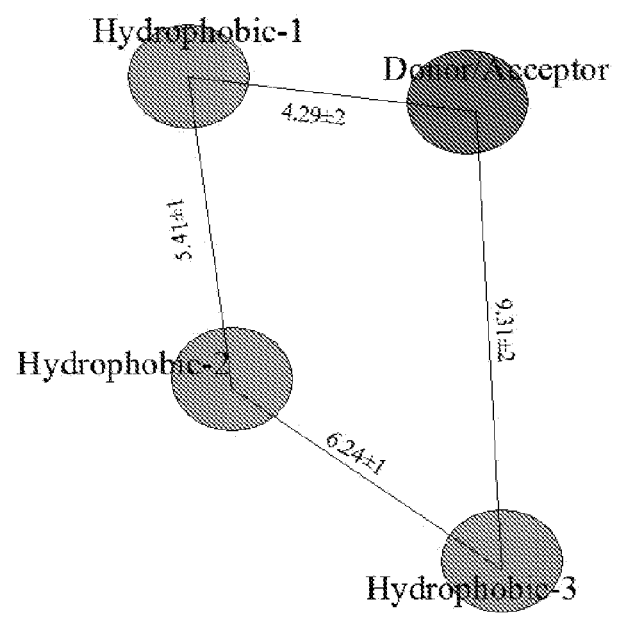
FIG. 2 is a four point structure based pharmacophore constructed by combining the interactions of MyoA tail with MyoA-tail Interacting Protein (MTIP)
Figure 3:
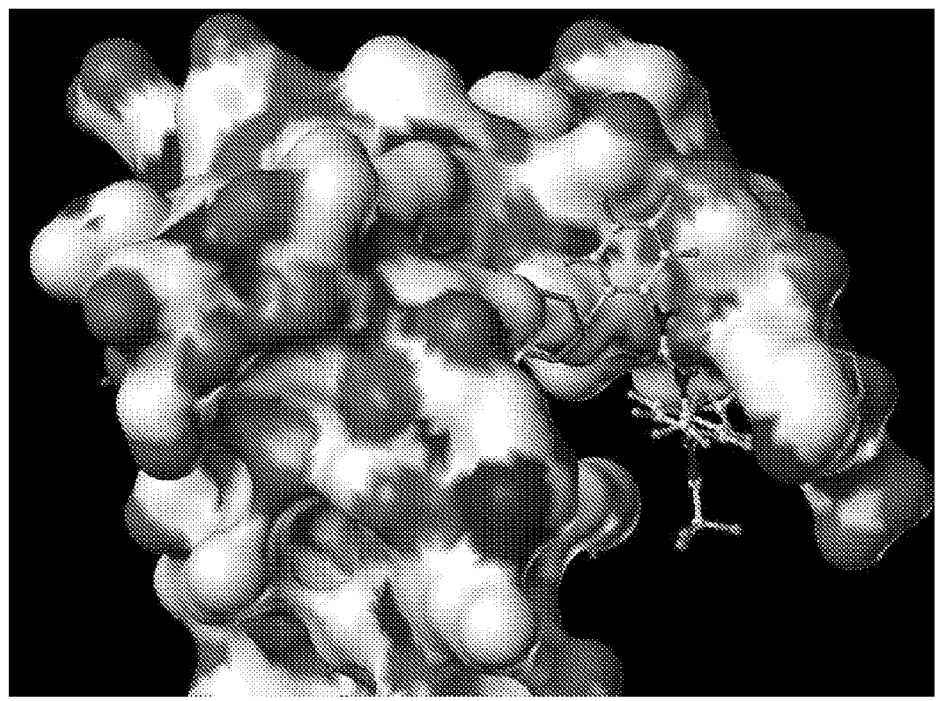
FIG. 3 depicts compound 416 (ball and stick) docked into the binding site of MTIP.

A four point structural pharmacophore was built based on the interaction mode of MyoA protein in complex with MTIP. (FIG. 2). The pharmacophore was screened against the National Cancer Institute (NCI) database of small molecules resulting in 42 compounds. These compounds were then docked and scored using GoldScore, Chemscore and an in-house customized scoring scheme. Three best ranking compounds (NCI-344032, NCI-146498 and NCI-377159) were chosen for further modeling. A recently published Hybrid structure based (HSB) scheme of virtual screening was used to identify commercially available small molecules that could potentially bind to MTIP. The HSB method is composed of 4 phases:

a) Development of an Enriched Database of Small Molecules that could Have a Better Potential to Bind to MTIP: The ligand based shape signature method was used to build this enriched database using the NCI compounds as query molecules. 2,638 commercially available molecules were identified to form the enriched database.

b) Screening Against the Combined Pharmacophore: A structural pharmacophore consisting of information from both MTIP and MyoA was built. (FIG. 1). Using this pharmacophore, the enriched database was screened using the molecular modeling program SYBYL (ver 7.1, UNITY module) and 40 compounds that strictly obeyed the pharmacophore were identified.

c) Docking and Scoring: These 40 hits were then docked into the binding site of MTIP-C subunit using program GOLD (ver 3.1). All of the docked complexes were scored using three different scoring functions namely GoldScore, Chemscore, and an in-house customized scoring function. The molecules were also screened for Absorption, Distribution, Metabolism, Excretion, and Toxicology (ADMET) properties using the program CHEMAXON. The molecules were then filtered based on their logP and molecular weight values leading to the final set of 28 compounds. FIG. 2 depicts the docking of compound 416 in the binding site of MTIP. The compound mimics the binding mode of the MyoA tail in MTIP by being hydrophobic like the MyoA helix and also compensating for the hydrophilic interactions through the reactive groups.

d) The final phase of HSB method involves experimental screening of the best ranking compounds against MTIP. Fifteen potential inhibitor compounds were selected by this technique, acquired, and assigned random numerical descriptors to facilitate biological evaluation against *P. falciparum* using a growth inhibition assay. $IC_{50}$ values were determined for promising candidate molecules.

Example 2

Growth Inhibition Assay (Series-1)

Synchronized (74% late trophozoites, 13% schizonts, 12% ring stages) *P. falciparum* strain 3D7 parasites were seeded at 2% parasitemia in 96-well plates and treated with varying concentration of the inhibitors as well as the solvent (DMSO) for 24 hours. [$^3$H]Hypoxanthine was added to the cultures and incubation was continued for an additional 24 hours. Incorporation of [$^3$H]hypoxanthine by the parasites was determined by liquid scintillation. Growth inhibition was assessed as the decrease in [³H]hypoxanthine incorporation in treated parasites relative to the control parasites treated with the solvent.

Figure 4:
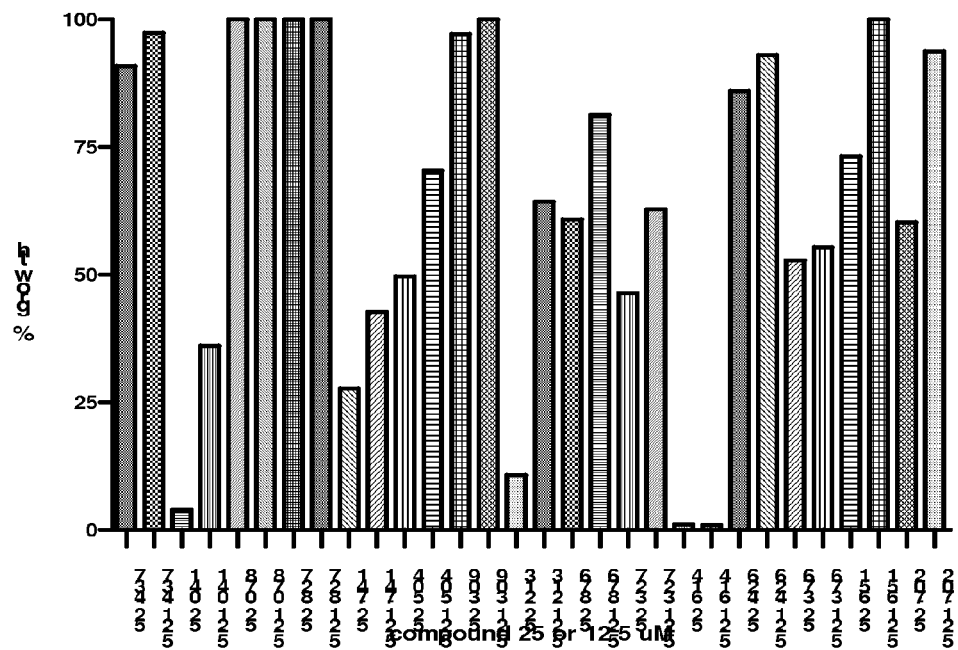
FIG. 4 is a chart depicting results from initial growth inhibition assays of potential inhibitors (series-1) of *P. falciparum;*
Figure 5:
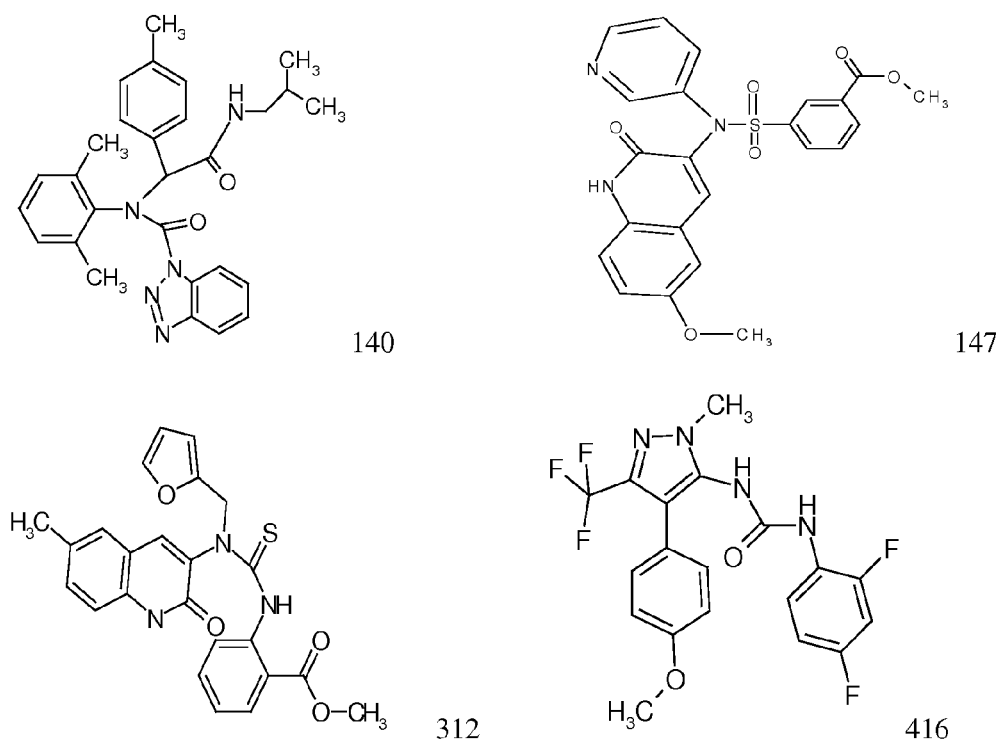
FIG. 5 provides structural drawings of compounds designated 146, 147, 312, and 416.
Figure 10A:
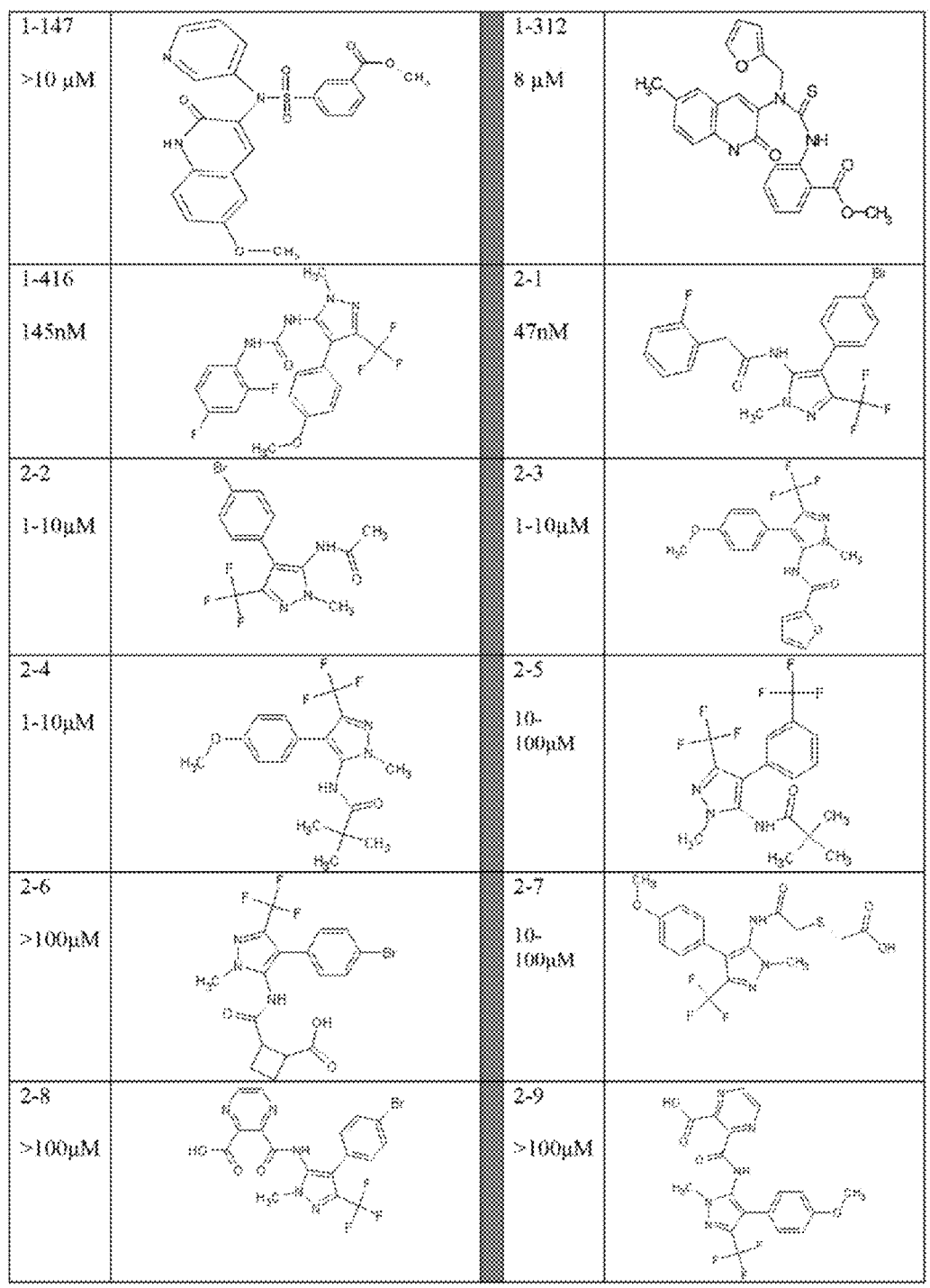
* and FIG. 10 is a listing of compounds tested for antiparasitic activity in this study with their series numbers, 2D structures, and $IC_{50}$ values.
Figure 10C:
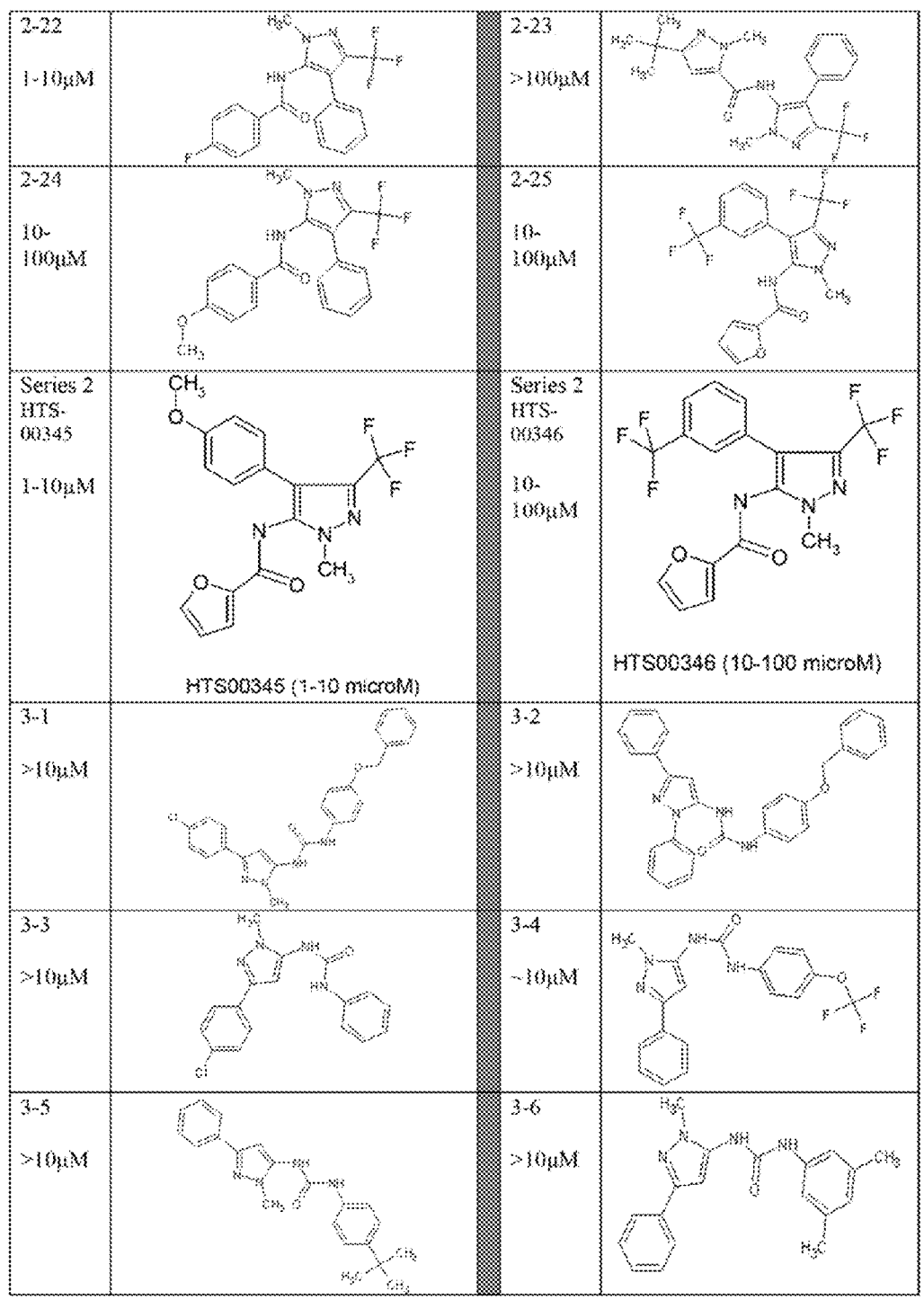
Figure 10D:
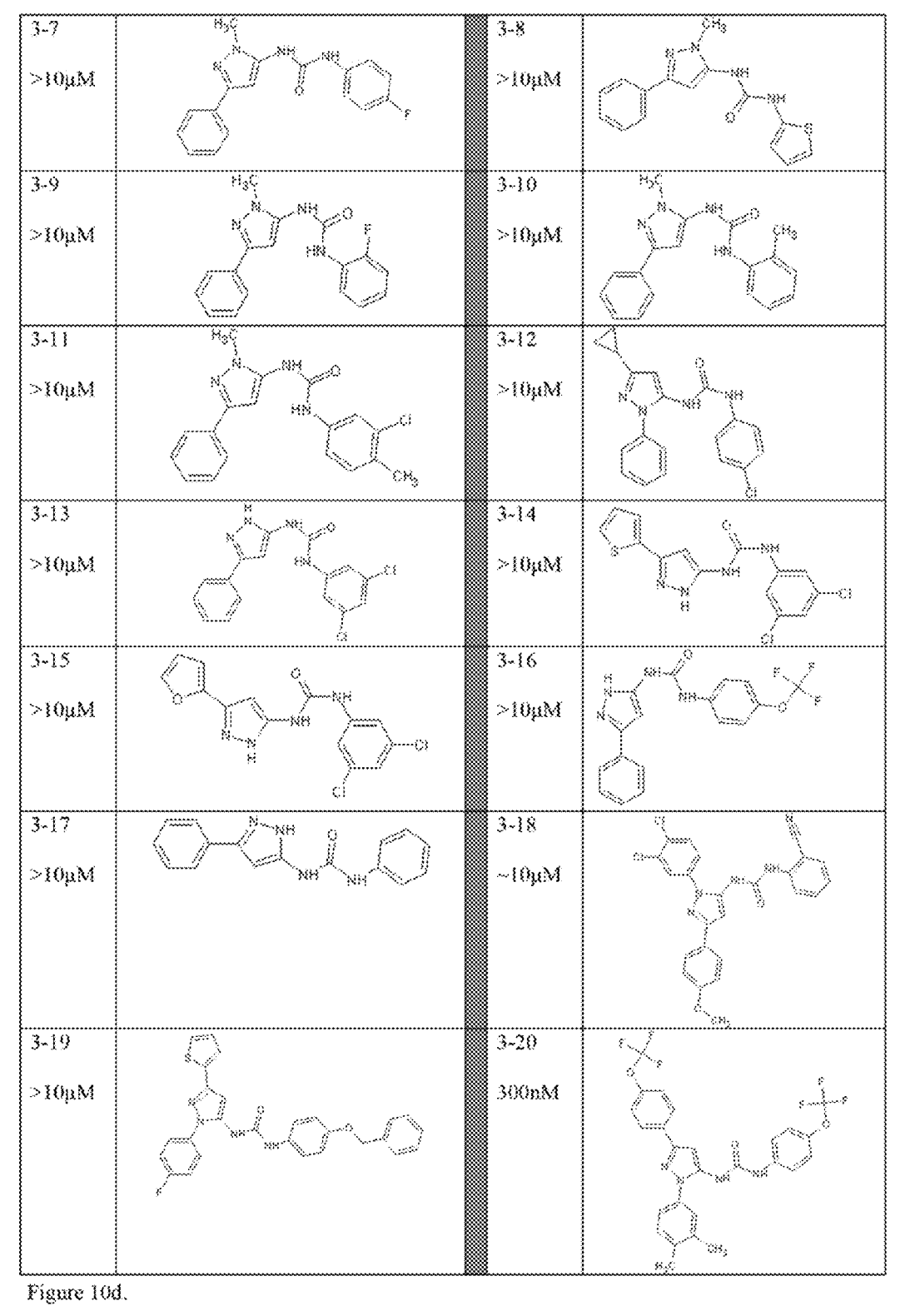
Figure 10E:
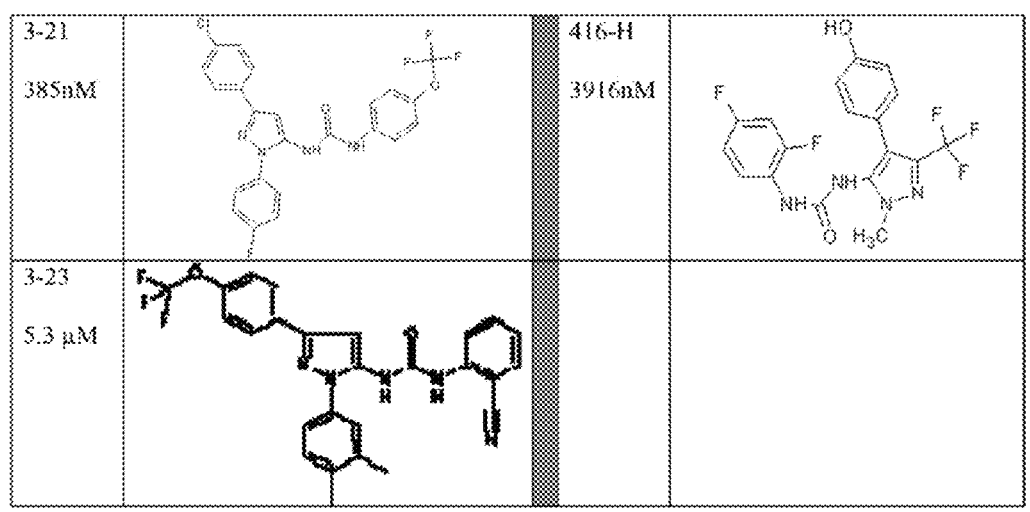

Each of the prospective 15 inhibitor compounds was tested at concentrations of 12.5 μM and 25 μM to find evidence of inhibitory activity. Results of these initial assays are summarized in FIG. 4. Each of the tested compounds is identified by a numerical code along the x-axis of the Figure. Significant growth inhibition (<50% growth @ 25 μM, or <25% growth @ 12.5 μM) was exhibited by four of these compounds: 140, 147, 312, and 416. The molecular structures of these four compounds are depicted in FIGS. 5 and 10.

Example 3

Dose Response Assays (Series-1)

Figure 6:
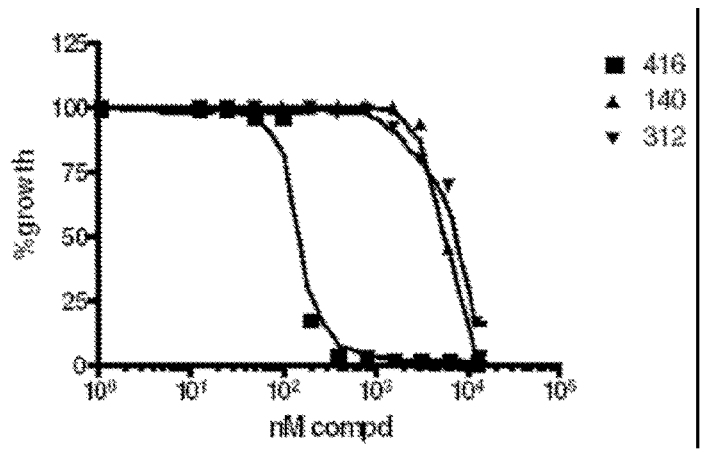
FIG. 6 is a plot of percent growth of *P. falciparum* as a function of various amounts of compounds 416, 140, and 312.
Figure 7A:
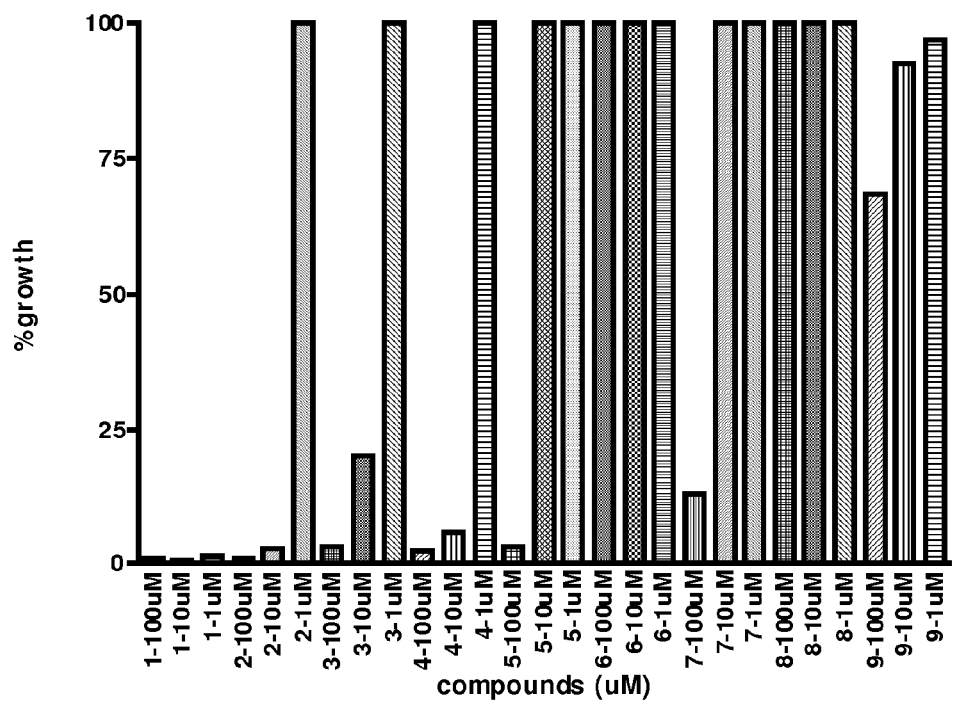
FIGS. 7*a-c* are charts depicting results from initial growth inhibition assays of potential inhibitors (series-2) of *P. falciparum;*
Figure 7B:
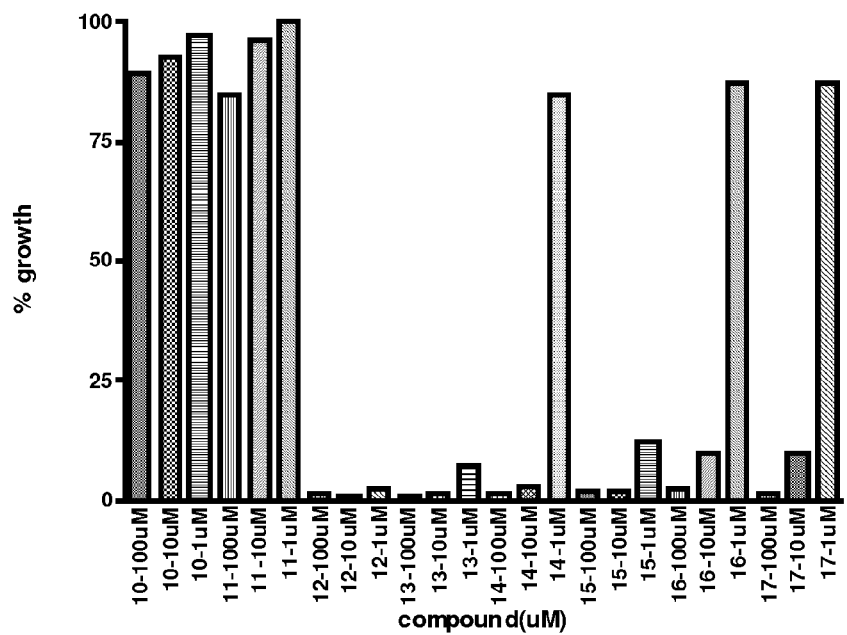
Figure 7C:
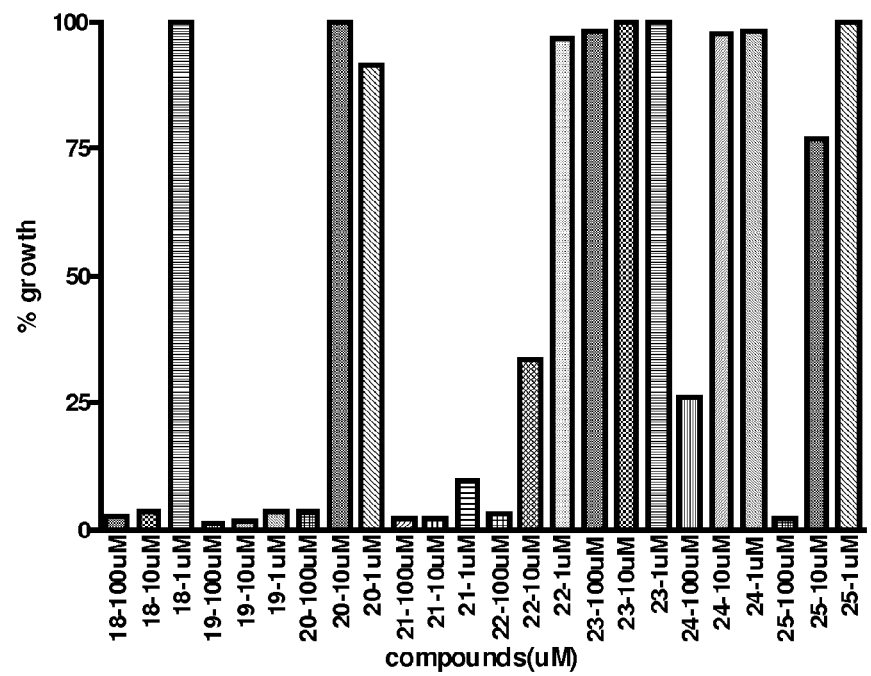

Three of the compounds from Example 2 (140, 312 and 416) showed growth inhibitory activity, and were tested more extensively to determine mid-point inhibitory concentrations ($IC_{50}$) by studying their effect on *P. falciparum* growth in human red cells as measured by incorporation of ³H-labeled hypoxanthine. The parasites in culture were exposed to serial dilutions of each compound. The parasites' ability to incorporate ³H-hypoxanthine was assessed. A range of compound concentrations was tested in 48-hour growth inhibition assays. The results of these experiments are given in FIGS. 6 and 10. Compound 416 was found to have $IC_{50}$ of approximately 100 nM.

Example 4

Drug-like Properties of Compound 416

The drug-like properties of Compound 416 were predicted using computational models. The following calculated values indicate that Compound 416 satisfies Lipinski's Rules and other conditions associated with orally bioavailable drugs.
Mol. Wgt=426.34
Rotatable Bonds=3-4
Hydrogen Bond Donor Atoms=2; Hydrogen Bond Acceptor Atoms=4
logP=3.41; logD=3.41 (at pH=7.4)
Polar Surface Area (PSA)=68.18 Å²

Example 5

Growth Inhibition Assay (Series-2)

Further in silico analysis was performed with Compound 416 as a lead compound. Electronic databases were queried for structural analogs of Compound 416. 25 additional compounds (series-2) were chosen and examined for their growth inhibition activity against *P. falciparum* as described in Example 2. Results from these studies are given in FIGS. 7*a-c* and 10. Compounds 1, 12, 13, 19 and 21 had inhibitory activities at concentrations below 1 μM.

Example 6

Dose Response Assays (Series-2)

Compounds 1, 12, 13, 19, and 21 were tested more extensively to determine mid-point inhibitory concentrations ($IC_{50}$) as described in Example 3. A multidrug-resistant *P. falciparum* strain was used as the test parasite. Compound 1 was found to have the lowest $IC_{50}$ value (47 nM), whereas compound 12 had $IC_{50}$ of 136 nM. Compounds 13, 19, and 21 had $IC_{50}$ of >250 nM.

Example 7

Growth Inhibition Assay (Series-3)

Figure 8:
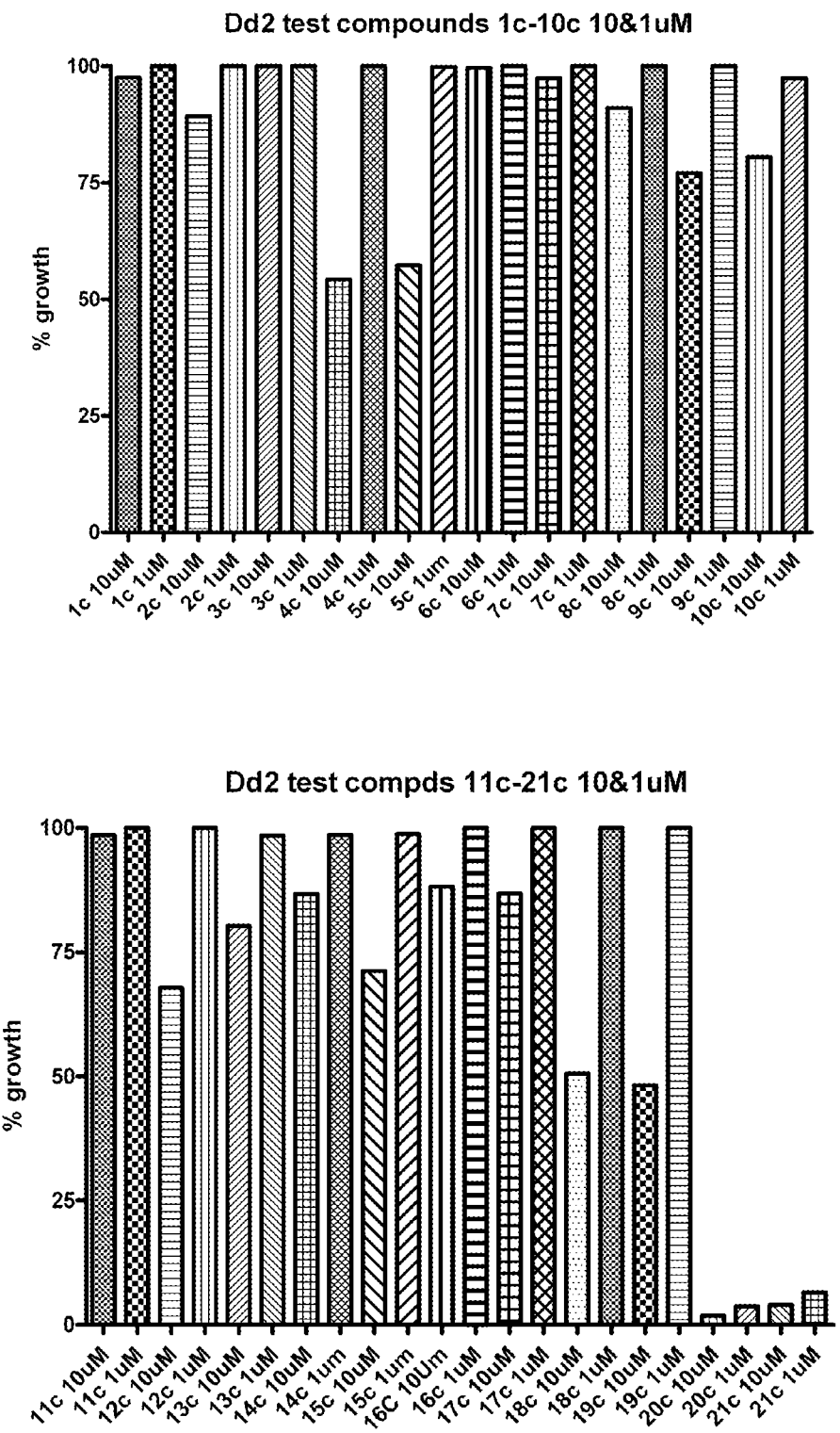
FIG. 8 provides charts depicting results from initial growth inhibition assays of potential inhibitors (series-3) of *P. falciparum;*

A third set of 21 compounds were identified based on the structure activity relationship developed from compounds belonging to series-1 and series-2. They were examined for their growth inhibition activity against *P. falciparum* as described in Example 2. Results from the study are shown in FIGS. 8 and 10. Compounds 20 and 21 had $IC_{50}$ values of ~300 nM and ~380 nM respectively.

Example 8

Figure 9:
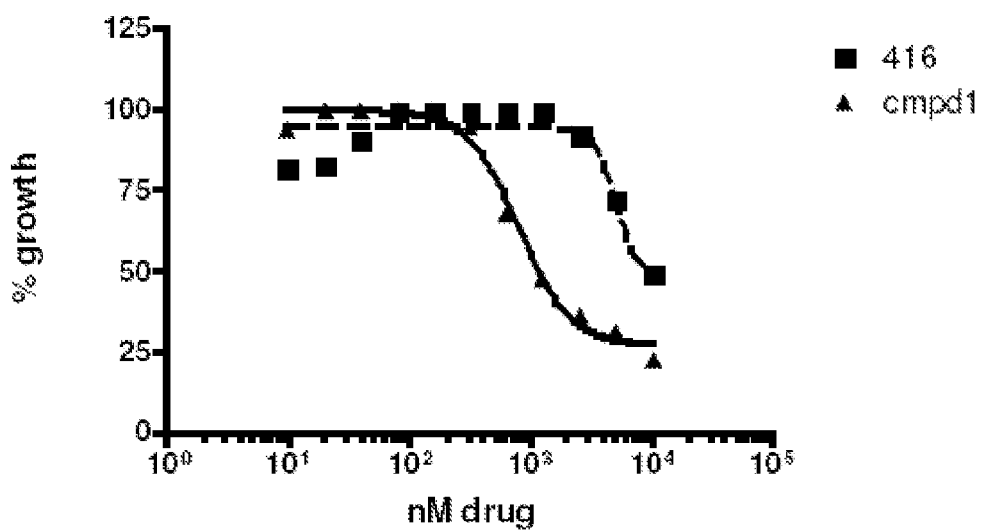
FIG. 9 depicts the in vitro activities of compounds 1 and 416 on *P. berghei* and *P. yoelii.
Figure 9:
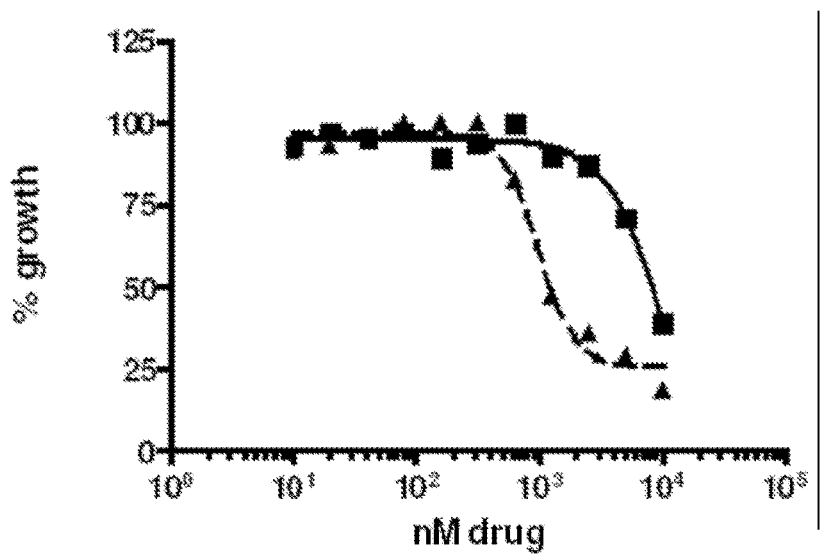

Rodent Parasite Study 24-hour metabolic incorporation assays using in vitro cultures of *P. yoelii* and *P. berghei* were carried out with varying concentrations of compounds 1 and 416. Results from these experiments are shown in FIG. 9. Compound 1 appears to be active against these parasites just as in *P. falciparum*. Compounds from series-3, namely compounds 20 and 21, had substantial activity against *P. berghei* and *P. yoelii* parasites, with their $IC_{50}$'s in the range of 300 to 500 nM. This study suggests that the pyrazole urea compounds do act on other species of the apicomplexan protozoa.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:
1. A method for treating an Apicomplexan parasite infection in a patient, said method comprising administering to a patient in need thereof an effective amount of a compound of Formula IV:

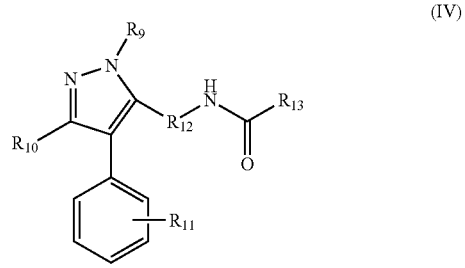

or a pharmaceutically acceptable salt thereof, wherein
$R_9$, $R_{10}$, and $R_{11}$ are independently selected from the group consisting of hydrogen, halogen, acetoxy, lower alkyl, lower haloalkyl, lower haloalkoxy, aryl, and lower alkoxy;
$R_{12}$ is a bond or; and
$R_{13}$ is selected from the group consisting of methyl, —C(CH₃)₃, —NHC(CH₃)₃, —C≡N, Hydroxyl,

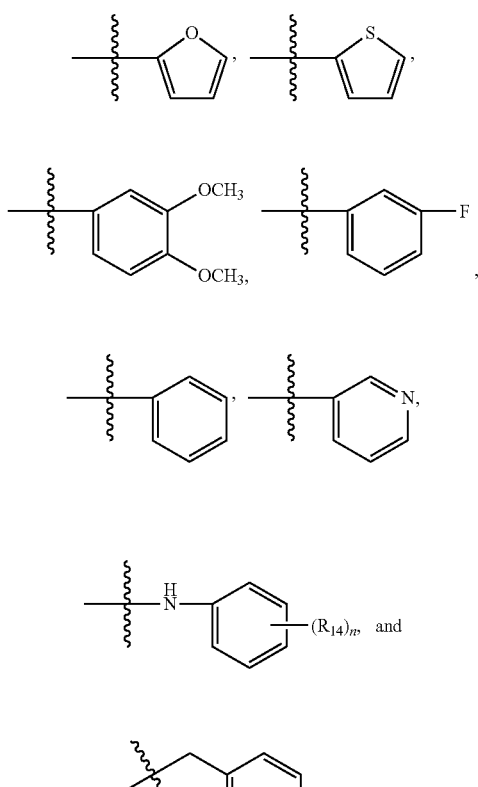
wherein $R_{14}$ is selected from the group consisting of hydrogen, halogen, acetoxy, lower alkyl, lower haloalkyl, lower haloalkoxy, aryl, and lower alkoxy and n is an integer from 1 to 3.
2. The method of claim 1 wherein the compound is selected from the group consisting of:
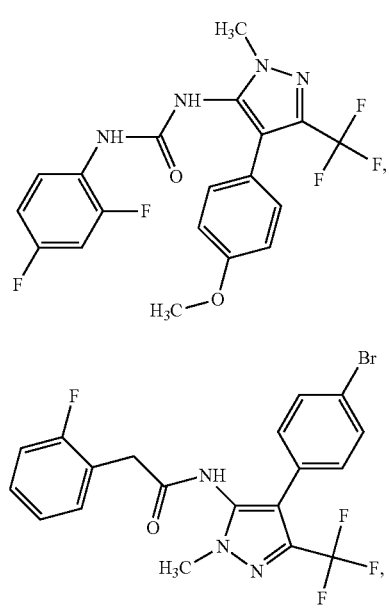
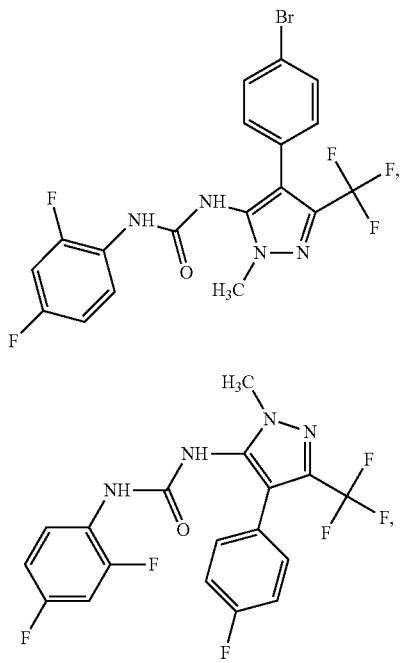

-continued

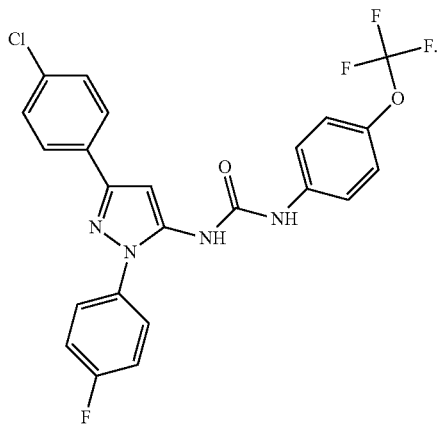
(XIV)

3. A method according to claim 1, wherein the Apicomplexan parasite is selected from the group consisting of *Toxoplasma, Plasmodium, Eimeria, Theileria, Babesia, Sarcocystis, Cryptosporidium, Cydospora, Isospora*, and *Neospora*.

4. The method of claim 3, wherein the Apicomplexan parasite is selected from the group consisting of *Plasmodium falciparum, Plasmodium vivax, Cryptosporidium parvum*, and *Cyclospora cayatanensis*.

5. The method of claim 2, wherein the compound is a compound of formula (VII):

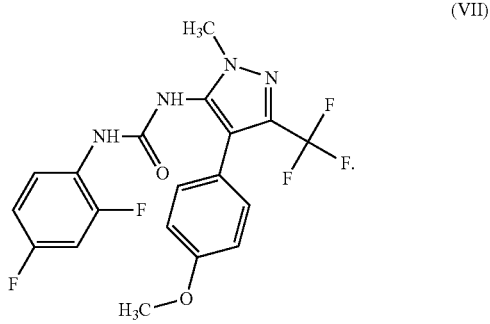 [SMILES: COc1ccc(-c2c(C(F)(F)F)nn(C)c2NC(=O)Nc2ccc(F)cc2F)cc1]
(VII)

6. The method of claim 2, wherein the compound is a compound of formula (VIII):

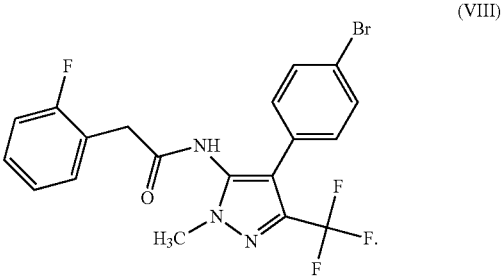 [SMILES: Cn1nc(C(F)(F)F)c(-c2ccc(Br)cc2)c1NC(=O)Cc1ccccc1F]
(VIII)

7. The method of claim 3, wherein the compound is a compound of formula (VII):

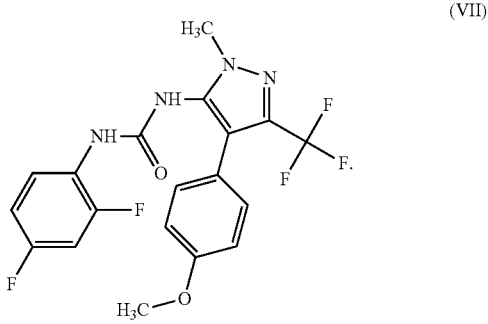 [SMILES: COc1ccc(-c2c(C(F)(F)F)nn(C)c2NC(=O)Nc2ccc(F)cc2F)cc1]
(VII)

8. The method of claim 3, wherein the compound is a compound of formula (VIII):

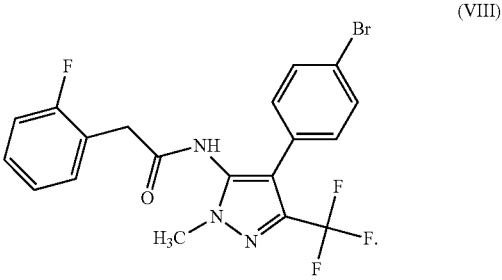 [SMILES: Cn1nc(C(F)(F)F)c(-c2ccc(Br)cc2)c1NC(=O)Cc1ccccc1F]
(VIII)

* * * * *